US006307156B1

(12) United States Patent
Avellanet

(10) Patent No.: US 6,307,156 B1
(45) Date of Patent: Oct. 23, 2001

(54) HIGH FLEXIBILITY AND HEAT DISSIPATING COAXIAL CABLE

(75) Inventor: Francisco J. Avellanet, Coral Gables, FL (US)

(73) Assignee: General Science and Technology Corp., Miami, FL (US)

( * ) Notice: Subject to any disclaimer, the term of this patent is extended or adjusted under 35 U.S.C. 154(b) by 0 days.

(21) Appl. No.: 09/484,819

(22) Filed: Jan. 18, 2000

Related U.S. Application Data

(63) Continuation-in-part of application No. 09/450,879, filed on Nov. 29, 1999, which is a continuation of application No. 08/843,405, filed on May 2, 1997, now Pat. No. 5,994,647.

(51) Int. Cl.$^7$ .............................. H01B 5/08; H01B 11/18

(52) U.S. Cl. .......................................... 174/128.1; 174/28

(58) Field of Search ............................. 174/128.1, 128.2, 174/125.1, 126.1, 28, 108, 102 R, 15.1

(56) References Cited

U.S. PATENT DOCUMENTS

| | | | |
|---|---|---|---|
| 1,943,086 | 12/1934 | McKnight | 173/264 |
| 1,943,087 | 1/1934 | Potter et al. | 173/264 |
| 2,140,174 | * 12/1938 | Smith | 174/28 X |
| 2,156,652 | 5/1939 | Harris | 57/145 |
| 2,204,737 | * 6/1940 | Swallow et al. | 174/28 |
| 2,274,031 | * 2/1942 | Bannon | 174/25 |
| 2,527,172 | * 10/1950 | Beaver et al. | 174/106 |
| 2,978,860 | 4/1961 | Campbell | 57/148 |
| 3,131,469 | 5/1964 | Glaze | 29/470.5 |
| 3,195,299 | 7/1965 | Dietz | 57/149 |
| 3,234,722 | 2/1966 | Gilmore | 57/145 |
| 3,352,098 | 11/1967 | Gilmore | 57/147 |
| 3,822,542 | 7/1974 | Naud et al. | 57/145 |
| 3,883,371 | 5/1975 | Geary | 148/32 |
| 3,955,390 | 5/1976 | Geary | 72/64 |
| 4,048,807 | * 9/1977 | Ellers et al. | 174/11 R X |
| 4,529,837 | 7/1985 | Borden | 174/128 |
| 4,654,477 | 3/1987 | Isoda | 174/128 R |
| 4,731,134 | 3/1988 | Alloin et al. | 156/53 |

(List continued on next page.)

FOREIGN PATENT DOCUMENTS

| | | |
|---|---|---|
| 197692 | 5/1923 | (GB) . |
| 278233 | 10/1927 | (GB) . |

OTHER PUBLICATIONS

Hesterlee et al., "Trapwire Constructions", Mar. 1997, Wire Technology International, pp. 51–53.*

*Primary Examiner*—Chau N. Nguyen
(74) *Attorney, Agent, or Firm*—David P Gordon; David S Jacobson; Thomas A Gallagher

(57) ABSTRACT

A coaxial cable includes an inner conductor made of a number of conductive strands which are twined to form a wire rope which is drawn through a die to reduce its diameter until the outer surface of the cable is substantially smooth and the cross section of the cable is substantially circular, an outer conductor concentrically around the inner conductor, and a dielectric between the inner and outer conductors. The strands of the cable may be a single metal or alloy wires, or may be plated wires. The outer conductor may be a highly flexible metallized tape which is helically wrapped around the dielectric. As such, the coaxial cable has substantially greater flexibility. According to a second embodiment, a coaxial cable includes inner and outer conductors, and a dielectric therebetween. The dielectric includes an outer cross-sectional shape which is preferably different from an inner cross-sectional shape of the outer conductor. As a result of the different cross-sectional shapes, channels are formed between dielectric and the outer conductor which facilitate cooling of the cable. According to a preferred aspect of the second embodiment, a cooling fluid is circulated throughout the channels to remove heat. The cooled coaxial cable provides a signal transmission medium with reduced high frequency signal attenuation.

41 Claims, 6 Drawing Sheets

U.S. PATENT DOCUMENTS

| | | | |
|---|---|---|---|
| 4,778,246 | 10/1988 | Carroll | 350/96.23 |
| 4,960,965 * | 10/1990 | Redmon et al. | 174/102 R |
| 4,987,274 * | 1/1991 | Miller et al. | 174/102 R |
| 5,349,133 * | 9/1994 | Rogers | 174/108 X |
| 5,389,736 * | 2/1995 | Ziemek et al. | 174/102 R X |
| 5,477,011 * | 12/1995 | Singles et al. | 174/102 R |
| 5,892,176 * | 4/1999 | Findlay et al. | 174/102 R X |

* cited by examiner

HIGH FLEXIBILITY AND HEAT DISSIPATING COAXIAL CABLE

This application is a continuation-in-part of U.S. Ser. No. 09/450,879, filed on Nov. 29, 1999, which is a continuation of U.S. Ser. No. 08/843,405, filed May 2, 1997, now U.S. Pat. No. 5,994,647 which are hereby incorporated by reference herein in their entireties.

BACKGROUND OF THE INVENTION

1. Field of the Invention

The invention relates to electrically conductive coaxial cable. More particularly, the invention relates to coaxial cables having low electrical resistance, high tensile strength, good flexibility, and which are capable of relatively high frequency signal transmission.

2. State of the Art

Wire is manufactured from ingots using a rolling mill and a drawing bench. The preliminary treatment of the material to be manufactured into wire is done in the rolling mill where white hot billets (square section ingots) are rolled to round wire rod. The action of atmospheric oxygen causes a coating of mill scale to form on the hot surface of the rod which must be removed. This descaling can be done by various mechanical methods (e.g., shot-blasting) or by pickling, i.e., immersion of the wire rod in a bath of dilute sulfuric or hydrochloric acid. After pickling, the wire rod may additionally undergo a jolting treatment which dislodges the scale loosened by the acid. The remaining acid is removed by immersion of the wire rod in lime water.

The actual process of forming the wire is called drawing and is carried out on the metal in a cold state with a drawing bench. Prior art FIG. 1 shows a simple drawing bench 10. The wire 12 is pulled through a draw plate 14 which is provided with a number of holes, e.g. 16, of various diameters. These holes taper from the diameter of the wire 12 that enters the hole to the smaller diameter of the wire 12' that emerges from the hole. The thick wire rod 12 is coiled on a vertical spool 18 called a swift and is pulled through the die by a rotating drum 20 mounted on a vertical shaft 22 which is driven by bevel gearing 24. The drum can be disconnected from the drive by means of a clutch 26. To pass a wire through a hole, the end of the wire is sharpened to a point and threaded through the hole. It is seized by a gripping device and rapidly pulled through the hole. This is assisted by lubrication of the wire. Each passage through a hole reduces the diameter of the wire by a certain amount. By successively passing the wire through holes of smaller and smaller diameter, thinner and thinner wire is obtained.

In the modern wire industry, instead of a draw plate, dies are used. Dies are precision-made tools, usually made of tungsten carbide for larger sizes or diamond for smaller sizes. The die design and fabrication is relatively complex and dies may be made of a variety of materials including single crystal natural or synthetic diamond, polycrystalline diamond or a mix of tungsten and cobalt powder mixed together and cold pressed into the carbide nib shape.

A cross section of a die is shown in prior art FIG. 2. Generally, the dies used for drawing wire have an outer steel casing 30 and an inner nib 32 which, as mentioned above, may be made of carbide or diamond or the like. The die has a large diameter entrance 34, known as the bell, which is shaped so that wire entering the die will draw lubricant with it. The shape of the bell causes the hydrostatic pressure to increase and promotes the flow of lubricant into the die. The region 36 of the die where the actual reduction in diameter occurs is called the approach angle. In the design of dies, the approach angle is an important parameter. The region 38 following the approach angle is called the bearing region. The bearing region does not cause diametric reduction, but does produce a frictional drag on the wire. The chief function of the bearing region 38 is to permit the conical approach surface 36 to be refinished (to remove surface damage due to die wear) without changing the die exit. The last region 40 of the die is called the back relief. The back relief allows the metal wire to expand slightly as the wire leaves the die. It also minimizes the possibility of abrasion taking place if the drawing stops or if the die is out of alignment with the path of the wire.

Although wire drawing appears to be a simple metalworking process, those skilled in the art will appreciate that many different parameters affect the physical quality of the drawn wire. Among these parameters, draw stress and flow stress play an important role. If these parameters are not carefully considered, the drawn wire may have reduced tensile strength. A discussion of the practical aspects of wire drawing can be found in Wright, Roger N., "Mechanical Analysis and Die Design", Wire Journal, October 1979, the complete disclosure of which is hereby incorporated by reference herein.

The wire forming processes described above may be used to form different kinds of wires including wires which are used to conduct electricity and wires which are used as structural supports. Generally, the most important physical characteristic of a wire used to conduct electricity is its electrical resistance. In addition, where wire is used as a signal transmission medium, the attenuation frequency characteristics of a wire are extremely important. In all types of wires, flexibility may also be an important characteristic, with increased flexibility facilitating the snaking of wire through a tortuous path.

Cables are a bundle of wire strands held together, and typically include wire strands twisted together into a rope. Generally, a cable exhibits much more flexibility than a single wire of comparable diameter. Thus, in both structural and electrical applications, where flexibility is important, stranded cables are generally used rather than single solid wires. Stranded cables also have the advantage that they do not kink as easily as solid wires and they can be connected to terminals by crimping. However, stranded cables have some disadvantages, including lower tensile strength and higher electrical resistance than solid wires of comparable diameter. In addition, the rough outer surface presented by stranded cables makes them more difficult to insulate than solid wires.

Prior art FIGS. 3 and 4 schematically illustrate an electrical transmission cable 50, in which several strands of wire are twined to produce a flexible cable having an overall diameter D, but which has a smaller cross sectional area than a solid wire with the same diameter. The cable 50 is shown consisting of seven wire strands 52, 54, 56, 58, 60, 62, 64 each having a diameter "d". In actual practice, an electrical transmission cable may consist of many more conductive strands and one or more steel core strands which serve to enhance the tensile strength of the cable. As shown, the seven strands are twined to form the conductive cable 50 having an overall diameter "D" which is approximately 2.15 d. However, the cross sectional area of the conductive cable 50, for purposes of computing the resistance (or conductance) of the cable is not as large as the cross sectional area of a solid wire having a diameter of 2.15 d. Thus, the stranded and twined cable 50 will have a higher resistance than a solid single strand of wire with the same cross sectional diameter.

Coaxial cable is another type of cable, and is suitable as a signal transmission medium. Coaxial cable generally consists of an unbalanced pair of conductors, in which an inner conductor is surrounded by an outer conductor (shielding layer), and the two conductors are held in a concentric relationship by a dielectric (insulator). The inner conductor is typically a single strand of drawn wire, while the outer conductor is typically a tubular braid of individually drawn wires or a conductive foil. The dielectric can be many different types including polyethylene, polyvinyl chloride, gas injected foams (e.g., nitrogen gas-injected foam polyethylene), other foams, Spirafil®, and air or another gas. Where the dielectric is air or another gas, the inner conductor is maintained in position by the use of discrete spacers. For long-distance telecommunication signal transmissions, coaxial cables are provided in two standard gauges. Small gauge cable includes an inner conductor having an outer diameter of approximately 0.047 inches, and an outer conductor having an outer diameter of 0.174 inches. Large gauge cable has an inner conductor having an outer diameter of approximately 0.104 inches and an outer conductor having an outer diameter of approximately 0.375 inches. The use of a solid wire inner conductor having a diameter of 0.047 inches or 0.104 inches limits the flexibility of the standard coaxial cables. However, unlike electrical transmission lines, a stranded cable is typically not suitable for the central conductor due to standard connectors adapted for terminating free ends of the cable. In addition, when carrying transmission signals, and particularly high frequency signals, coaxial cables tend to generate heat, which is undesirable.

The expansion of the telecommunications industry has created a greater need for coaxial cables exhibiting good signal transmission characteristics, particularly at higher frequencies. In addition, such cables should be highly flexible and preferably capable of dissipating heat.

SUMMARY OF THE INVENTION

It is therefore an object of the invention to provide an coaxial cable which is highly flexible.

It is also an object of the invention to provide a coaxial cable which has low electrical resistance.

It is another object of the invention to provide a coaxial cable which dissipates heat.

It is a further object of the invention to provide a coaxial cable which has reduced high frequency signal attenuation.

In accord with these objects which will be discussed in detail below, a coaxial cable according to the invention includes an inner conductor, an outer conductor (or shielding layer) concentrically around the inner conductor, and a dielectric (insulator) between the inner and outer conductors. According to a first preferred aspect of a first embodiment of the invention, the inner conductor is a cable comprised of a number of conductive strands which are twined to form a wire rope which is drawn through a die to reduce its diameter until the outer surface of the cable is substantially smooth and the cross section of the cable is substantially circular. The strands of the cable may be a single metal or alloy wires, or may be plated wires. In addition, a combination of differently comprised strands may be used in the rope. According to a presently preferred embodiment, the rope is drawn through a die to reduce its diameter by at least approximately 9%, and preferably successively drawn through at least two dies of decreasing diameter to decrease its overall diameter by at least 18%. More preferably, the wire rope is drawn successively through four dies of decreasing diameter so that the overall diameter of the wire rope is reduced by at least 30–40%. The resulting cable has much of the flexibility advantage of a twined wire rope and much of the low resistance advantage of a solid conductor. In addition, the successive drawing causes the inner conductor cable to have a substantially smooth outer surface which facilitates extruding the dielectric layer over the inner conductor. Moreover, the tensile strength of the drawn cable is significantly better than a twisted rope of comparable diameter. Furthermore, an inner conductor produced thereby exhibits reduced parasitic reactance and reduced signal attenuation relative to twisted ropes. According to a second preferred aspect of the invention, the outer conductor may be a highly flexible metallized tape which is helically wrapped around the dielectric. As such, the coaxial cable has excellent flexibility.

According to a second embodiment of the invention, a coaxial cable includes inner and outer conductors, and a dielectric layer therebetween. The dielectric layer includes an outer cross-sectional shape which is different from an inner cross-sectional shape of the outer conductor. The outer cross-sectional shape of the dielectric is preferably triangular, rectangular, or oval. The outer conductor is preferably made from a cross-sectional shape maintaining construction, such as a woven wire braid or flexible metal tube. The shapes for the inner cross-section of the outer conductor is preferably circular. As a result of the different cross-sectional shapes, channels are formed between dielectric layer and the outer conductor which facilitate cooling of the cable. According to a preferred aspect of the second embodiment, a cooling fluid such as liquid nitrogen is circulated throughout the channels to remove heat. The cooled coaxial cable provides a signal transmission medium with reduced high frequency signal attenuation.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
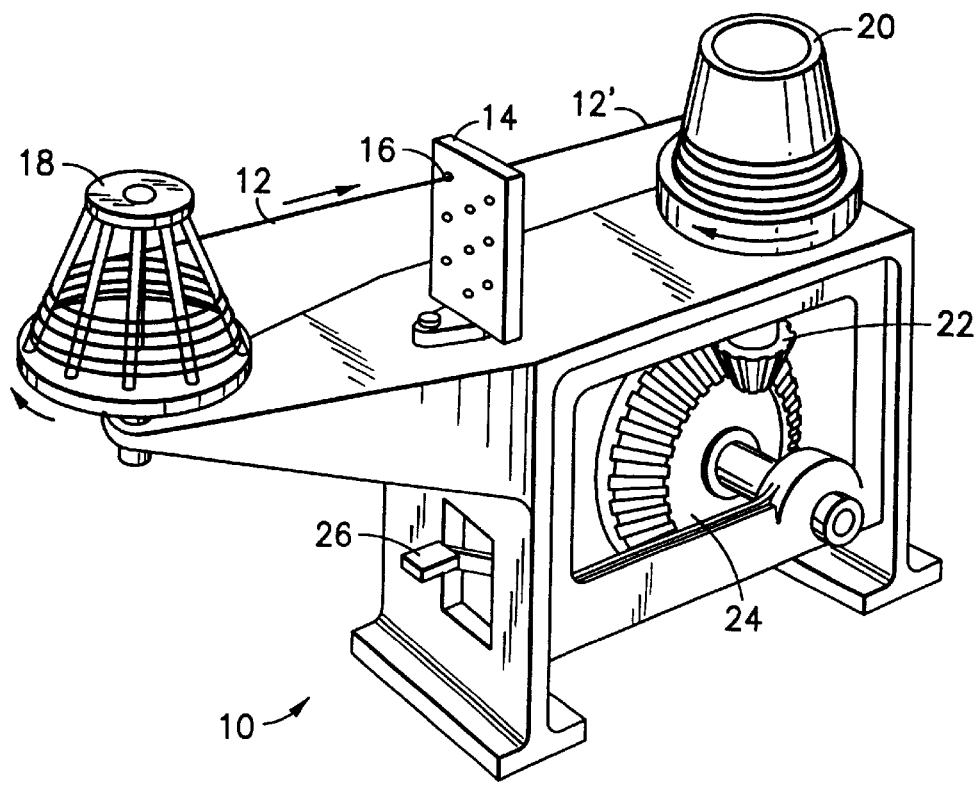
FIG. 1 is a schematic perspective view of a prior art wire drawing apparatus.
Figure 2:
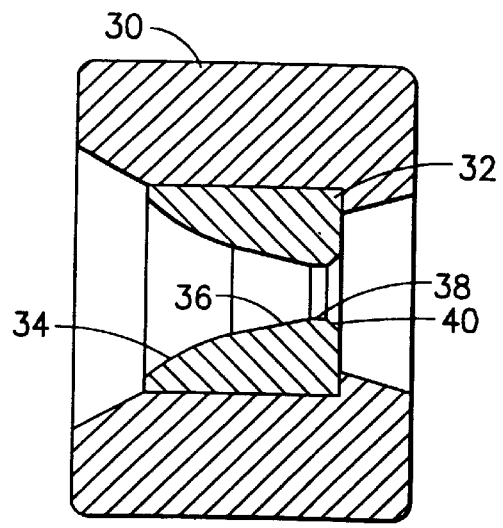
FIG. 2 is a schematic sectional view of a prior art drawing die.
Figure 3:
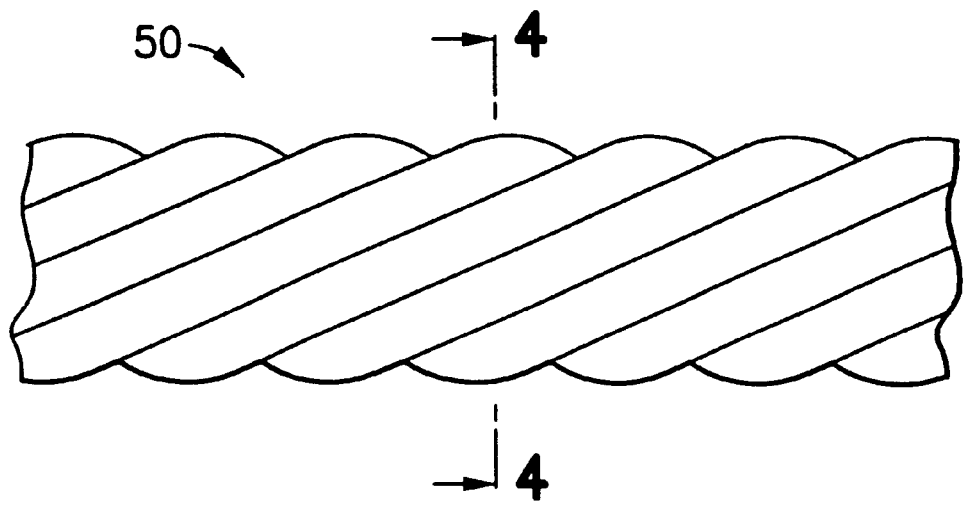
FIG. 3 is a broken schematic side elevation view of a prior art wire rope conductor.
Figure 4:
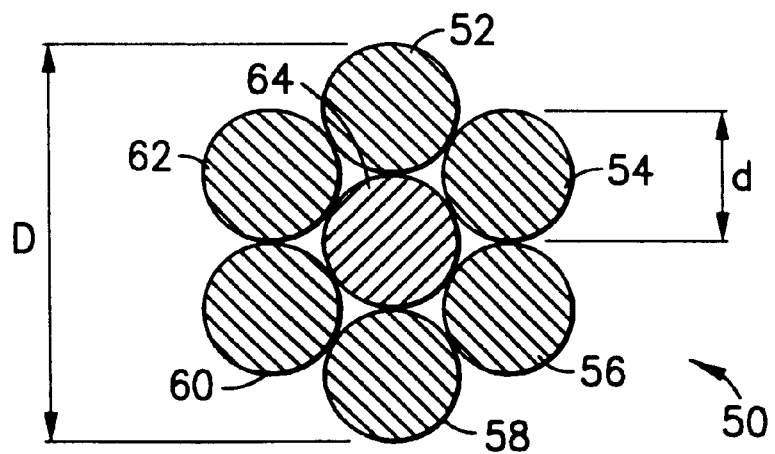
FIG. 4 is a cross-sectional view of the prior art wire rope conductor taken along line 4—4 in FIG. 3.
Figure 5:
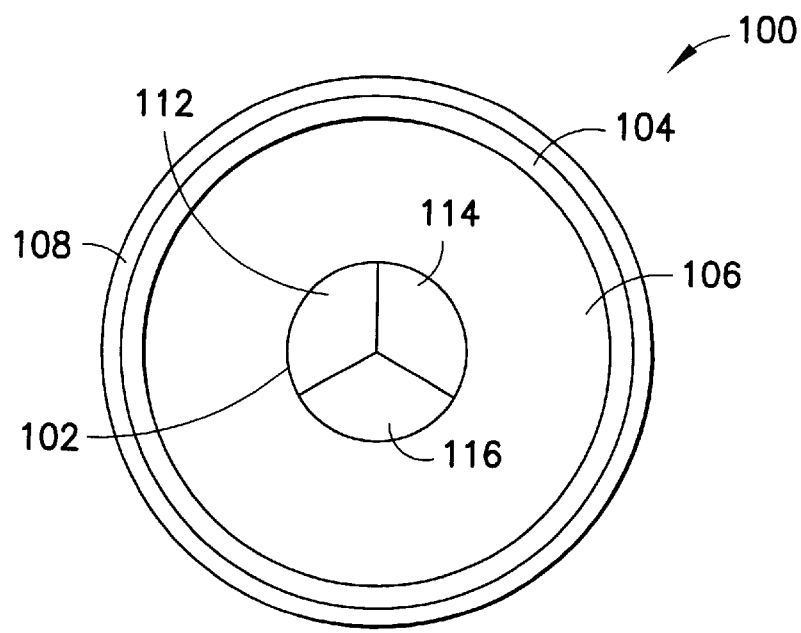
FIG. 5 is a cross-sectional view of a coaxial cable according to a first embodiment of the invention.

Referring now to FIG. 5, a coaxial cable 100 includes an inner conductor 102, an outer conductor 104 (or shielding layer) concentrically around the inner conductor 102, and a dielectric (insulator) layer 106 between the inner and outer conductors. Preferably, an outer insulating layer 108 is provided over the outer conductor 104. According to a first preferred aspect of a first embodiment of the invention, the inner conductor 102 is a cable comprised of a number of conductive strands which have been stranded (twined) to form a wire rope, using a tubular strander, a twister, or any other stranding means. The wire rope is then drawn through a die (or swaged) to form a cable with a reduced, substantially smooth diameter and a cross section which is generally circular.

It is noted that twining electrically conductive strands and drawing the strands through at least one die will result in a cable which has different properties than a cable produced by another method which does not require drawing the strands through a die. For example, at least on a microscopic level and possibly on a macroscopic level, a twisted and drawn cable is structurally different than cable manufactured by rolling strands together. In particular, rolling wires together into a cable forms ridges about the sides of the cable, and the discontinuous orifice formed by rollers causes radial material flow forming undesirable ridges on the cable. These ridges on rolled cable can potentially cause an uneven density of the cable which can affect how the electrons flow on the outer surface of cable. In addition, rolled cables are crushed and therefore have different surface grain structures than cables comprised of drawn strands of wire. Also, it is believed that the surface grain structure of rolled cables has a negative effect on skin effect during A.C. current flow.

Figure 6:
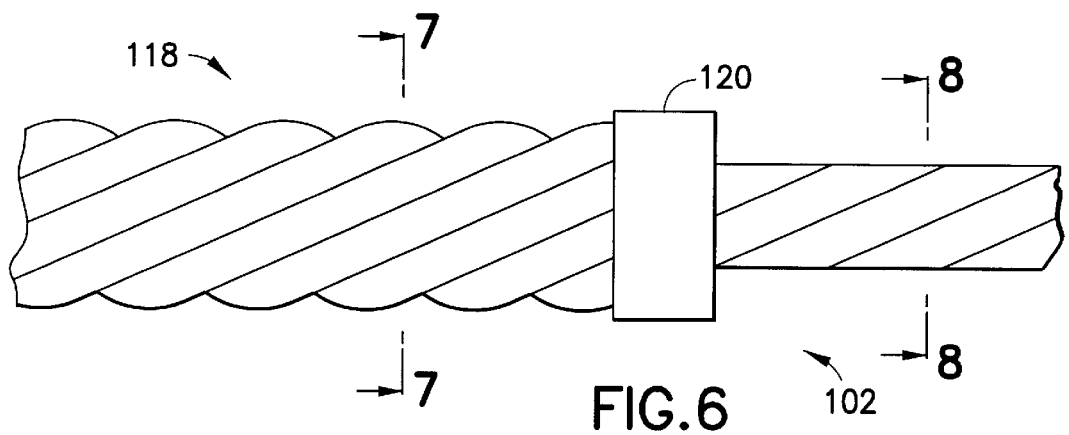
FIG. 6 is a schematic view of the manufacture of the inner conductor of the coaxial cable of FIG. 5.
Figure 7:
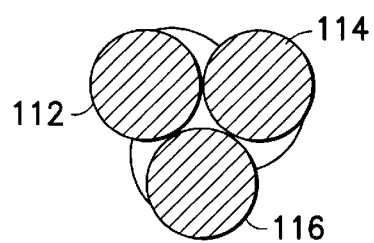
FIG. 7 is a cross-sectional view taken along line 7—7 in FIG. 6.
Figure 8:
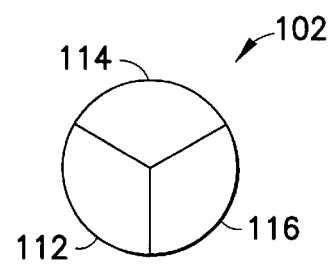
FIG. 8 is a cross-sectional view taken along line 8—8 in FIG. 6.

More particularly, referring to FIGS. 6 through 8, the wire rope used to manufacture the inner conductor 102 includes several conductive strands, e.g. strands 112, 114, 116, which are twined together to form the wire rope 118. The wire rope 118 is pulled through a die 120 using known wire drawing methods and apparatus whereby its diameter is decreased. Preferably, the wire rope 118 is successively drawn through a plurality of dies of decreasing diameter to form a cable. During the drawing process, the conductors 112, 114, 116 are plastically deformed. After the drawing is completed, the cable of the inner conductor 102 assumes a substantially circular cross section as shown in FIG. 8, but maintains the flexibility advantage of a wire rope; that is, a twisted and drawn cable of any diameter is more flexible that a solid wire of the same material at the same diameter. In addition, drawing the cable 102 through dies burnishes the surface of the cable to provide a substantially smooth surface which facilitates the extrusion of the dielectric layer 106 over the inner conductor. The dielectric layer may be polyethylene, polyvinyl chloride, gas-injected foam, other foam, or Spirafil®. In addition, the dielectric may be air or another fluid, preferably in conjunction with dielectric spacers.

According to the presently preferred embodiment, the wire rope 118 is successively pulled through four dies of decreasing diameter. The resulting inner conductor cable 102 has a diameter which is preferably approximately at least 30–40% smaller than the diameter of the wire rope 118. However, successively drawing the wire rope through at least one die to reduce the diameter at least approximately 9%, and more preferably through at least two dies to reduce the diameter at least 18% is within the scope of the invention. The process of twisting conductive wire strands into a rope and drawing the rope into a conductive cable is disclosed in greater detail in co-owned U.S. Ser. No. 08/963, 686, filed Nov. 4, 1997, which is hereby incorporated by reference herein in its entirety.

The strands 112, 114, 116 of the wire rope 118 may be made from a single metal, e.g., copper or silver, or an alloy, e.g., a copper-nickel alloy such as constantan or Inconel™. In addition, each strand may be a plated or otherwise coated wire, e.g., silver-plated copper or copper-plated stainless steel, which preferably enhances the conductivity of the strand relative to the base material but at a reduced cost relative to making the strand entirely from the plating material. In addition, a combination of differently comprised strands may be used in the rope.

The first embodiment of the invention will now be described in more detail with respect to several examples.

EXAMPLE 1

Still referring to FIG. 5, three strands of 0.0285 inch copper wire 112, 114, 116 are twisted to form a wire rope wherein no one wire forms a core wire. The rope is continuously twisted and drawn through two successive dies (each providing a nine percent reduction in diameter for a total of eighteen percent reduction in diameter) and collected on a take up spool to provide an inner conductor 102 in which none of the wires forms a core wire. The twisted and drawn inner conductor has a diameter of approximately 0.047 inch. A polytetrafluoroethylene insulating layer 106 is provided over the inner conductor 102. A flexible copper-plated stainless steel tube 104, preferably having a thickness of 0.015–0.032 inch, and having an outer diameter of approximately 0.174 inch is provided over the insulating layer 106. The resulting coaxial cable is flexible and has excellent transmission capability.

EXAMPLE 2

Figure 9:
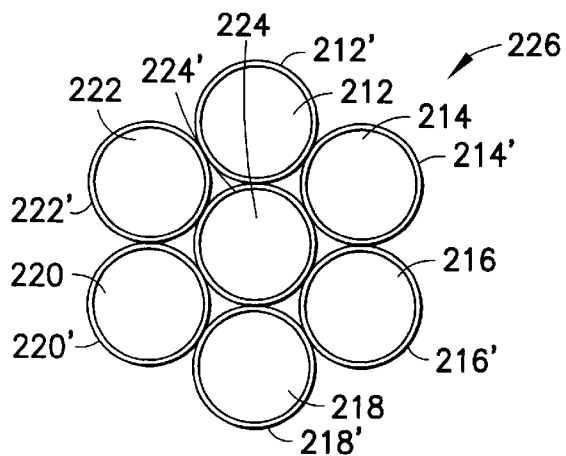
FIG. 9 is an enlarged cross-section of a wire rope for forming an inner conductor according to a second example of a coaxial cable according to the first embodiment of the invention.
Figure 10:
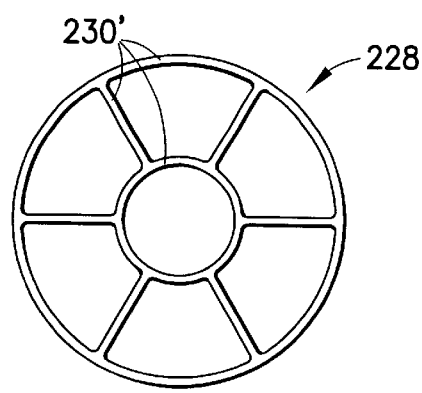
FIG. 10 is an enlarged cross-section of a twisted and drawn cable inner conductor made from the wire rope of FIG. 9.
Figure 11:
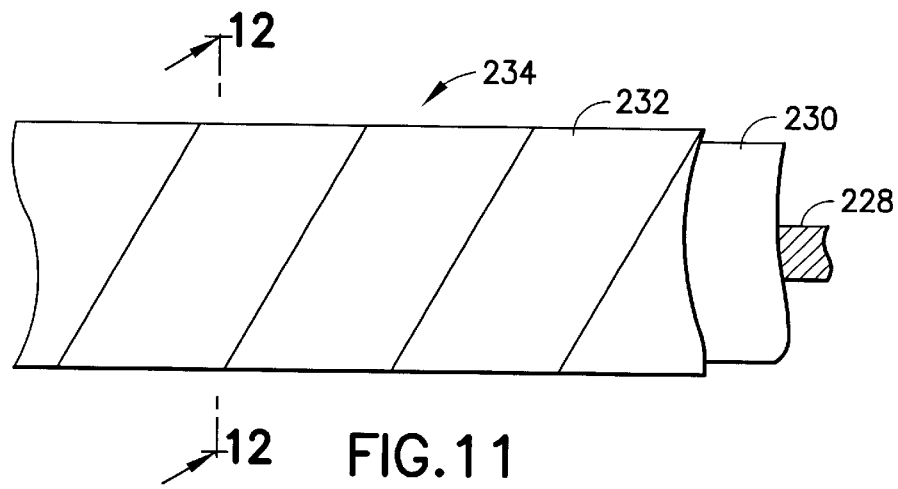
FIG. 11 is a broken side elevation of the second example of the first embodiment of the coaxial cable of the invention.
Figure 12:
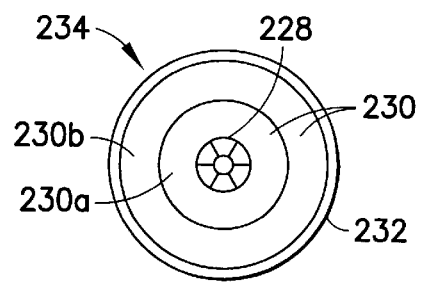
FIG. 12 is a cross-section through line 12—12 of FIG. 11.

Referring to FIGS. 9 and 10, six strands of 25 gauge (0.0179 inch) oxygen free copper wire 212, 214, 216, 218, 220, 222, each plated in 40 microns of silver 212', 214', 216', 218', 220', 222', are twisted around a single 25 gauge strand of oxygen free copper wire 224, plated in 40 microns of silver 224', to form a wire rope 226. The rope 226 is continuously twisted with a lay length of 0.5 inch and drawn through successive dies onto a take up spool until several hundred or thousand feet of cable 228 are obtained. The cable was then annealed. The cable after drawing has a diameter of 0.0435 inch. The highly conductive silver plating 23' encases and surrounds the drawn copper strands. The resulting cable 228 is highly flexible and has a relatively low resistance of 5.60 ohms per one thousand feet. Referring to FIGS. 11 and 12, a tubular insulating layer 232 is extruded over the cable 230. The insulating layer 230 is a coextruded dielectric layer in which each layer 230a, 230b is made from polyethylene, but has a different cell structure. The inner dielectric layer 230a has a smaller, more compact cell structure and is therefore less flexible, while the outer dielectric layer has a larger cell structure and is more compressible and flexible. An outer conductive shielding layer 232, approximately 0.162 inch in diameter and approximately 0.0025 inch thick, is provided over the insulating layer 230 to form a coaxial cable 234. The conductive layer 232 is preferably an aluminum foil which is laminated to a highly flexible polypropylene film and helically wrapped around the insulating layer 230. The resulting coaxial cable is highly flexible. The coaxial cable of the example was compared to a coaxial cable having a solid copper core inner conductor, but otherwise similarly constructed, and a coaxial cable having an inner conductor including a plurality of stranded copper wires, but otherwise similarly constructed. The solid copper core coaxial cable failed after 67 flexing cycles and the stranded copper core cable failed after 103 flexing cycles. However, the coaxial cable of the invention, with twisted and drawn inner conductor, failed only after flexing through 135 cycles, lasting thirty percent longer than the stranded core cable and one hundred percent longer than the solid core cable. In addition, the coaxial cable has excellent transmission characteristics with reduced high frequency signal attenuation.

EXAMPLE 3

Six strands of 32 gauge (0.0080 inch) tin-plated copper wires, having a plating thickness of 15 microns, are twisted around a single strand of 32 gauge tin-plated copper wire, plated in silver', to form a wire rope. The wires are stranded with a 0.5 inch lay in a tubular strander. The stranded rope has an outside diameter of 0.201 inch (24 gauge). The rope is then drawn to reduce its diameter to 0.159 inch (26 gauge); i.e., a twenty percent reduction in diameter. Drawing is performed by passing the rope through a reducing die twice, such that the diameter is first reduced by ten percent to 0.181 inch, and then reduced by twelve percent to 0.159 inch. Alternatively, compaction may be performed by reduction of twenty percent in a single die pass, or by passing the rope through two to six successive dies. The resulting compacted core is insulated with a dielectric, and an outer conductive foil is helically wrapped around the insulation.

EXAMPLE 4

Figure 13:
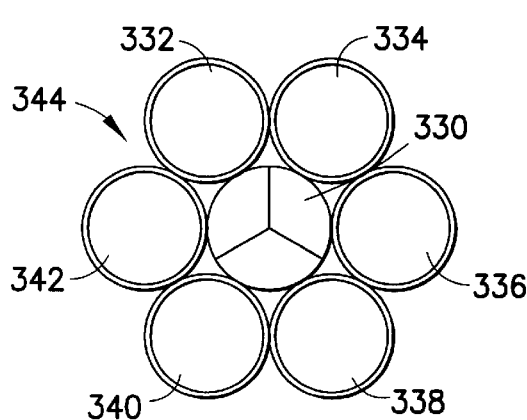
FIG. 13 is a cross-section of a wire rope used to form a coaxial cable according to a third example of the first embodiment of the invention.
Figure 14:
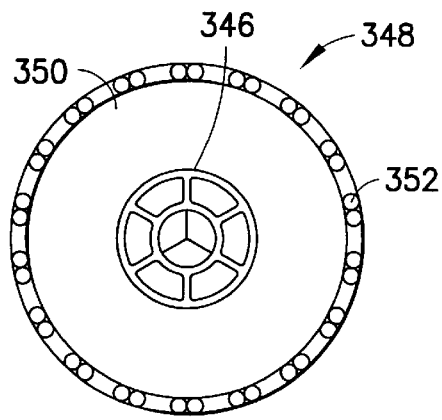
FIG. 14 is a cross-section of a coaxial cable including the wire rope of FIG. 13.

Three strands of silver are twisted to form a wire rope. The rope is continuously twisted and drawn through successive dies onto a take up spool until several hundred or thousand feet of a first cable 302 are obtained. Referring to FIG. 13, then six strands of silver-plated copper wire 332, 334, 336, 338, 340, 342 are twisted around the first cable 302, with the first cable positioned as a central core, to form a wire rope 344. Turning now to FIG. 14, the strands are drawn through successive dies onto a take up spool and form an inner conductor 346 of the cable having an outer diameter of 0.104 inches. A foam dielectric insulating layer 350 is extruded over the inner conductor. A tubular braid 352 having a diameter of approximately 0.375 inches and comprised of silver-plated copper wires extends around the insulating layer 350. The resulting coaxial cable has high flexibility for a respective gauge, and excellent transmission characteristics.

Figure 15:
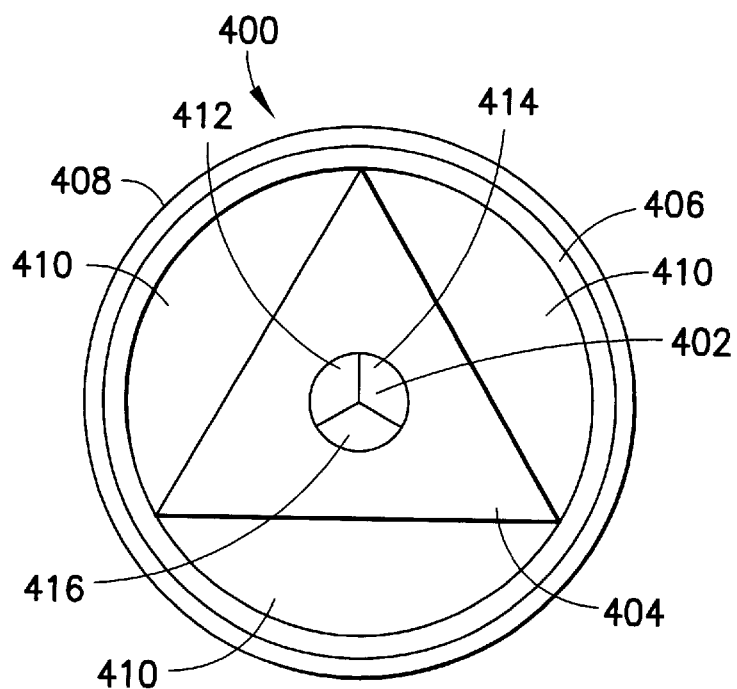
FIG. 15 is a cross-section of a coaxial cable according to a second embodiment of the invention.

Turning now to FIG. 15, a second embodiment of the invention is shown. The coaxial cable 400 includes an inner conductor 402, which is either a twisted and drawn cable as described above with respect to the first embodiment, a stranded rope, or a single wire strand. A dielectric layer 404 is provided, preferably by extrusion, over the inner conductor, and an outer conductor 406 is provided around the dielectric layer. According to the invention, the dielectric layer 404 includes an outer cross-sectional shape which is different from an inner cross-sectional shape of the outer conductor 406. The outer cross-sectional shape of the dielectric is preferably triangular, rectangular, or oval. The outer conductor is preferably made from a shape maintaining construction, such as a woven wire braid or flexible metal tube, and the inner cross-sectional shape of the outer conductor is preferably circular. The outer conductor is preferably coated in an outer insulating layer 408.

As a result of the relatively different cross-sectional shapes of the dielectric layer 404 and the outer conductor 406, channels 410 are formed between the dielectric layer and the outer conductor. The channels 410 may be filled with air to facilitate cooling of the cable. More preferably, a low temperature cooling fluid, such as liquid nitrogen, is circulated throughout the channels to dissipate heat. As it is believed that heat generation is a factor in signal attenuation at high frequency signal transmission, the cooled coaxial cable 400 provides a signal transmission medium with reduced high frequency signal loss.

The second embodiment is now described with respect to several exemplar embodiments.

EXAMPLE 5

Still referring to FIG. 15, three strands 412, 414, 416 of silver-coated copper wire are twisted to form a wire rope. The rope is continuously twisted and drawn and is an inner conductor 402 of the coaxial cable 400. The outer diameter of the inner conductor is approximately 0.047 inches. A plastic insulating layer 404 having a triangular cross-section is extruded over substantially the entire length of the inner conductor 402 such that the inner conductor is not exposed. A copper-coated stainless steel tubular cylinder 406 with an outer diameter of approximately 0.174 inches is provided over the insulating layer 404. Cooling channels 410 are formed between outer conductive layer and the insulating layer and filled with liquid nitrogen. The resulting coaxial cable is highly flexible, and has excellent transmission capability with reduced high frequency signal attenuation.

EXAMPLE 6

Figure 16:
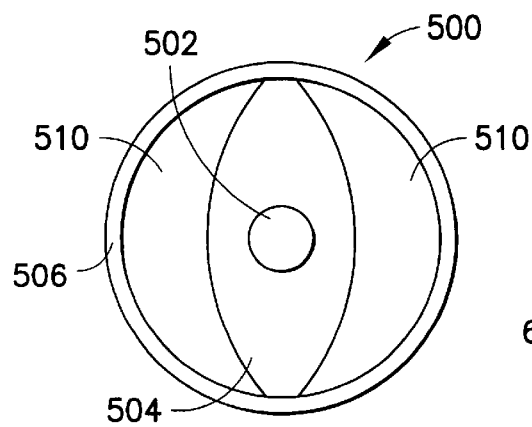
FIG. 16 is a cross-section through a coaxial cable according to a second example of the second embodiment of the invention.

Referring now to FIG. 16, a coaxial cable 500 includes a copper wire inner conductor 502, a PTFE insulating layer 504 extruded over the inner conductor and having an outer oval shape, and a cylindrical metallic outer conductor 506. Cooling channels 510 are formed between by the insulating layer and the outer conductor, and filled with liquid nitrogen.

EXAMPLE 7

Figure 17:
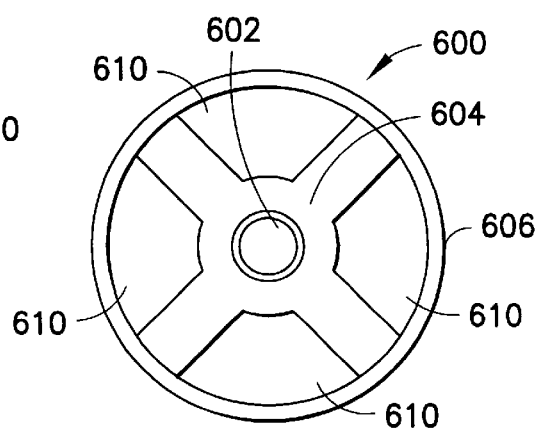
FIG. 17 is a cross-section through a coaxial cable according to a third example of the second embodiment of the invention.

Referring now to FIG. 17, a coaxial cable 600 includes a silver wire inner conductor 602, a polyethylene insulating layer 604 extruded over the inner conductor and having a generally cross-like shape, and a copper outer conductor 606 having a circular inner shape. Cooling channels 610 are formed between by the insulating layer and the outer conductor.

There have been described and illustrated herein several embodiments of a coaxial cable and a method of making it. While particular embodiments of the invention have been described, it is not intended that the invention be limited thereto, as it is intended that the invention be as broad in scope as the art will allow and that the specification be read likewise. Thus, while a particular number of strands for twisted and drawn inner conductors have been disclosed, it will be appreciated that a different number of strands could be utilized. Also, while it is preferable to helically twist the strands, it will be recognized that other types of twining of strands could be used with similar results obtained. Moreover, while particular configurations have been disclosed in reference to the number of dies used and the reduction in diameter of the rope/cable, it will be appreciated that other configurations could be used as well. Furthermore, while particular materials have been disclosed for the construction of conductive inner and outer conductors, and the dielectric layer, other materials may be used. Also, while an aluminum foil on a flexible polypropylene film base is disclosed as a conductive shielding layer, it will be appreciated that other metal foils, preferably having a thickness of 0.0001 to 0.005 inch, may be laminated on other polymer base films, such as polyester. Further, while particular plating thicknesses have been disclosed, it will be appreciated that other plating thicknesses can be used, preferably in the range of 10 to 60 microns. In addition, while particular preferred diameters of the inner and outer conductors have been disclosed, it will be appreciated that the inner and outer conductors may have other diameters. In addition, while several dielectric materials have been disclosed in the examples, it will be appreciated that the dielectric could be air or a fluid coolant, e.g., liquid nitrogen. In addition, while several dielectric extrusions over the entire length have been disclosed, discontinuous spacers of the same or other shapes in conjunction with air or another fluid could also be used. Further, while one coextruded dielectric is disclosed in which the different layers have different cell structures, it will be appreciated that coextruded dielectric layers of the same or different materials may be provided over the inner conductor to provide the dielectric layer with desired properties: density, flexibility, cell structure, insulation factor, etc., or a combination thereof. Also, while a flexible cable is preferred for many applications, it will be appreciated that the cable may be made less flexible, and even rigid, by selection of rigid dielectric, outer conductor, and insulative jacket materials. Further, the inner conductor may be comprised of a twisted and drawn copper-clad steel cable. In addition, while particular features and preferred aspects have been disclosed in respective embodiments, it will be appreciated that each of the disclosed features and aspects may be otherwise combined into other embodiments of coaxial cables in accord with the invention. Further, the coaxial cable of the invention can be used in any application in which coaxial cables are used; for example, the cables may be used in telecommunications, the broadcast arena (studio, control room, post production), performance arts (microphone cables, guitar cables, mixers, recording equipment connection, public address systems, etc.), and patch cord cables. It will therefore be appreciated by those skilled in the art that yet other modifications could be made to the provided invention without deviating from its spirit and scope as claimed.

What is claimed is:

1. An electrically conductive coaxial cable, comprising:
   a) a first plurality of twined electrically conductive strands drawn through a plurality of successive dies of decreasing diameter to form an inner conductive cable;
   b) an outer conductor coaxially configured with said inner conductive cable; and
   c) a dielectric between said inner conductive cable and said outer conductor.

2. A coaxial cable according to claim 1, wherein:
said inner conductive cable has a substantially circular cross section with a diameter which is at least approximately 9% smaller than an overall cross sectional diameter of said first plurality of twined electrically conductive strands.

3. A coaxial cable according to claim 1, wherein:
said inner conductive cable has a substantially circular cross section with a diameter which is at least approximately 18% smaller than an overall cross sectional diameter of said first plurality of twined electrically conductive strands.

4. A coaxial cable according to claim 1, wherein:
said inner conductive cable has a substantially circular cross section with a diameter which is at least approximately 24% smaller than an overall cross sectional diameter of said first plurality of twined electrically conductive strands.

5. A coaxial cable according to claim 1, wherein:
said inner conductive cable has a substantially circular cross section with a diameter which is at least approximately 30% smaller than an overall cross sectional diameter of said first plurality of twined electrically conductive strands.

6. A coaxial cable according to claim 1, wherein:
no one of said first plurality of electrically conductive strands forms a central core of said inner conductive cable.

7. A coaxial cable according to claim 1, wherein:
one of said first plurality of electrically conductive strands forms a central core of said inner conductive cable.

8. A coaxial cable according to claim 1, wherein:
said inner conductive cable includes a central core comprised of a second plurality of twined electrically conductive strands which has been drawn through a plurality of successive dies of decreasing diameter.

9. A coaxial cable according to claim 1, wherein:
at least one of said first plurality of twined electrically conductive strands includes a first conductive material coated with a second conductive material.

10. A coaxial cable according to claim 9, wherein:
said second conductive material has greater conductance than said first conductive material.

11. A coaxial cable according to claim 1, wherein:
at least one of said first plurality of conductive strands is made of a different composition than another of said conductive strands.

12. A coaxial cable according to claim 1, wherein:
said first plurality of twined electrically conductive strands includes exactly six strands twined around a central core strand.

13. A coaxial cable according to claim 1, wherein:
said outer conductor is covered with an extruded insulator.

14. A coaxial cable according to claim 1, wherein:
said outer conductor is a conductive tape.

15. A coaxial cable according to claim 1, wherein:
said outer conductor is a braid.

16. A coaxial cable according to claim 1, wherein:
said outer conductor is a flexible conductive tube.

17. A coaxial cable according to claim 1, wherein:
said dielectric comprises a substantially non-conducting fluid.

18. A coaxial cable according to claim 1, wherein:
said dielectric further comprises spacers.
19. A coaxial cable according to claim 1, wherein:
said dielectric is a solid, said outer conductor has an inner cross-sectional shape, and said dielectric has an outer cross-sectional shape which is different than said inner cross-sectional shape such that at least one channel is provided between said dielectric and outer conductor.
20. A coaxial cable according to claim 19, wherein:
said outer cross-sectional shape is one of substantially triangular, substantially oval, and substantially cross-shaped, and
said inner cross-sectional shape is substantially circular.
21. A coaxial cable according to claim 19, wherein:
a cooling fluid is provided in said at least one channel.
22. A coaxial cable according to claim 1, wherein:
said dielectric includes coextruded layers in which each of said layers has different structure.
23. An electrically conductive coaxial cable, comprising:
a) an inner conductor comprised of a first plurality of twined electrically conductive strands drawn through a plurality of successive dies of decreasing diameter;
b) an outer conductor coaxially configured with said inner conductor, said outer conductor having an inner cross-sectional shape; and
c) a dielectric layer between said inner conductor and said outer conductor, said dielectric layer having an outer cross-sectional shape different than said inner cross-sectional shape such that at least one channel is formed between said dielectric layer and said outer conductor.
24. A coaxial cable according to claim 23, further comprising:
d) a cooling fluid provided in said at least one channel.
25. A coaxial cable according to claim 23, wherein:
said outer cross-sectional shape is one of substantially triangular, substantially oval, and substantially cross-shaped, and
said inner cross-sectional shape is substantially circular.
26. A coaxial cable according to claim 23, wherein:
said outer conductor is a flexible conductive tube.
27. A coaxial cable according to claim 23, wherein:
said outer conductor is a copper-coated stainless steel tube.
28. A coaxial cable according to claim 23, wherein:
said inner conductor is comprised of a first plurality of twined electrically conductive strands drawn through a plurality of successive dies of decreasing diameter.
29. A coaxial cable according to claim 23, wherein:
said inner conductor has a substantially circular cross section with a diameter which is at least approximately 18% smaller than an overall cross sectional diameter of said first plurality of twined electrically conductive strands.
30. A coaxial cable according to claim 23, wherein:
said dielectric layer is a coextrusion.
31. A method of making a conductive coaxial cable, comprising:
a) twining a first plurality of electrically conductive strands to form a wire rope;
b) drawing said wire rope successively through a plurality of dies of decreasing diameter to form an inner conductor;
c) providing a dielectric about said inner conductor; and
d) providing an outer conductor about said dielectric.
32. A method according to claim 31, wherein:
said wire rope is successively drawn such that said inner conductor has a substantially circular cross section with a diameter which is at least approximately 18% smaller than an overall cross sectional diameter of said first plurality of electrically conductive strands.
33. A method according to claim 31, wherein:
no one of said first plurality of electrically conductive strands forms a central core of said wire rope.
34. A method according to claim 31, wherein:
said dielectric is extruded over said inner conductor.
35. A method according to claim 31, wherein:
said dielectric is a solid having an outer cross-sectional shape and said outer conductor has an inner cross-sectional shape which is different than said outer cross-sectional shape.
36. A method according to claim 35, wherein:
said outer cross-sectional shape of said dielectric material is one of substantially triangular, substantially oval, and substantially cross-shaped, and
said inner cross-sectional shape of said outer conductor is circular.
37. A method according to claim 31, further comprising:
e) providing an insulative coating over said outer conductor.
38. A method according to claim 31, wherein:
at least one of said first plurality of conductive strands is made of a different composition than another of said conductive strands.
39. A method according to claim 31, wherein:
at least one channel is formed between said dielectric material and said outer conductor.
40. A method according to claim 39, further comprising:
d) providing a cooling fluid in said at least one channel.
41. A method according to claim 40, wherein:
said cooling fluid is liquid nitrogen.

* * * * *